United States Patent
Jang et al.

(10) Patent No.: US 9,285,332 B2
(45) Date of Patent: *Mar. 15, 2016

(54) LOW POWER CONSUMPTION TYPE GAS SENSOR AND METHOD FOR MANUFACTURING THE SAME

(71) Applicant: KOREA INSTITUTE OF SCIENCE AND TECHNOLOGY, Seoul (KR)

(72) Inventors: Ho Won Jang, Daegu (KR); Seok Jin Yoon, Seoul (KR); Jin Sang Kim, Seoul (KR); Chong Yun Kang, Seoul (KR); Ji Won Choi, Seoul (KR); Hi Gyu Moon, Gyeonggi-do (KR)

(73) Assignee: KOREA INSTITUTE OF SCIENCE AND TECHNOLOGY, Seoul (KR)

(*) Notice: Subject to any disclaimer, the term of this patent is extended or adjusted under 35 U.S.C. 154(b) by 0 days.

This patent is subject to a terminal disclaimer.

(21) Appl. No.: 14/250,821

(22) Filed: Apr. 11, 2014

(65) Prior Publication Data

US 2014/0217404 A1 Aug. 7, 2014

Related U.S. Application Data

(63) Continuation-in-part of application No. 13/542,874, filed on Jul. 6, 2012, now Pat. No. 8,785,924.

(30) Foreign Application Priority Data

Dec. 12, 2011 (KR) .................. 10-2011-0132714

(51) Int. Cl.
*H01L 29/49* (2006.01)
*G01N 27/12* (2006.01)
(Continued)

(52) U.S. Cl.
CPC .............. *G01N 27/127* (2013.01); *B82Y 15/00* (2013.01); *B82Y 40/00* (2013.01)

(58) Field of Classification Search
CPC ............................ G01N 27/127; B82Y 15/00
See application file for complete search history.

(56) References Cited

U.S. PATENT DOCUMENTS 4,781,798 A 11/1988 Gough
7,976,950 B2 7/2011 Okai et al.
(Continued)

FOREIGN PATENT DOCUMENTS

JP 05-179439 A 7/1993
JP 10-010048 A 1/1998
(Continued)

OTHER PUBLICATIONS

USPTO RR dated Apr. 26, 2013 in connection with U.S. Appl. No. 13/542,874.
(Continued)

*Primary Examiner* — Michael Shingleton
(74) *Attorney, Agent, or Firm* — Ladas & Parry LLP

(57) ABSTRACT

The present disclosure provides a gas sensor including: a substrate; an electrode formed on the substrate; and a gas-sensing layer formed on the electrode, wherein the gas-sensing layer is a self-heating nanocolumnar structure having nanocolumns formed on the electrode and inclined with respect to the electrode with an angle of 60-89° and gas diffusion pores formed between the nanocolumns. The gas sensor according to the present disclosure requires no additional heater since it self-heats owing to the nanocolumnar structure and exhibits superior gas sensitivity even when no heat is applied from outside. Also, it can be mounted on mobile devices such as mobile phones because it consumes less power.

12 Claims, 14 Drawing Sheets

(51) Int. Cl.
*B82Y 15/00* (2011.01)
*B82Y 40/00* (2011.01)

(56) References Cited

U.S. PATENT DOCUMENTS

| | | |
|---|---|---|
| 7,989,851 B2 | 8/2011 | Lu et al. |
| 2007/0210349 A1 | 9/2007 | Lu et al. |
| 2011/0008245 A1 | 1/2011 | Park et al. |
| 2012/0051976 A1 | 3/2012 | Lu et al. |
| 2012/0266658 A1 | 10/2012 | Akiyama et al. |
| 2013/0061660 A1 | 3/2013 | Kasama et al. |
| 2013/0075690 A1 | 3/2013 | Briman et al. |
| 2013/0078476 A1 | 3/2013 | Riman et al. |
| 2013/0146865 A1 | 6/2013 | Jang et al. |
| 2013/0209781 A1 | 8/2013 | Bellman et al. |

FOREIGN PATENT DOCUMENTS

| | | | |
|---|---|---|---|
| JP | 2002-170557 | A | 6/2002 |
| KR | 100316389 | B1 | 11/2001 |
| KR | 100812357 | B1 | 3/2008 |
| KR | 1020090046179 | A | 5/2009 |
| KR | 100932596 | B1 | 12/2009 |
| KR | 1020100067972 | A | 6/2010 |
| KR | 100989611 | B1 | 10/2010 |
| KR | 1020110056694 | A | 5/2011 |

OTHER PUBLICATIONS

USPTO NFOA dated Sep. 9, 2013 in connection with U.S. Appl. No. 13/542,874.

USPTO NOA mailed Mar. 31, 2014 in connection with U.S. Appl. No. 13/542,874.

LOW POWER CONSUMPTION TYPE GAS SENSOR AND METHOD FOR MANUFACTURING THE SAME

CROSS-REFERENCE TO RELATED APPLICATIONS

This application is a continuation-in-part of application Ser. No. 13/542,874, filed 6 Jul. 2012, and all the benefits accruing therefrom under 35 U.S.C. §119, the contents of which in its entirety are herein incorporated by reference.

BACKGROUND

1. Field

The present disclosure relates to a low power consumption type gas sensor and a method for manufacturing the same. More particularly, the present disclosure relates to a low power consumption type gas sensor self-heating and having superior gas sensitivity even when no heat is applied from outside and consuming less power, and a method for manufacturing the same.

2. Description of the Related Art

Gas sensors for detecting toxic gas, explosive gas, environmentally harmful gas, etc. are important in many fields including health care, national defense, counter-terrorism and environment. Researches are consistently ongoing on the gas sensors. In particular, researches are being carried out on the semiconductor gas sensor wherein gas-sensitive metal oxide film is used.

In general, a semiconductor gas sensor comprises a substrate, an electrode formed on the substrate, and a gas-sensing layer formed on the electrode. Recently, efforts are being made to improve gas sensitivity by increasing the specific surface area of the gas-sensing layer of the semiconductor gas sensor. For instance, Korean Patent Publication No. 10-2010-0067972 (Patent document 1) and Korean Patent Publication No. 10-2011-0056694 (Patent document 2) disclose semiconductor gas sensors wherein the gas-sensing layer is formed as nanofibers.

Since the semiconductor gas sensor operates on a simple principle, is compact in volume and costs little, it is expected to be capable of replacing the existing electrochemical or optical gas sensors.

Furthermore, if a semiconductor gas sensor having high sensitivity for the gas to be detected and consuming less power could be manufactured, it may be mounted on a mobile phone or other mobile devices, thereby further enhancing the functionality of the mobile devices.

However, no gas sensor with excellent light transmittance in the visible region without sacrificing performance has been reported as yet. In addition, despite the many advantages over the electrochemical or optical gas sensors, the existing semiconductor gas sensors are not widely used for practical applications because an additional heat source is necessary. That is to say, the existing semiconductor gas sensor has good gas sensitivity only when heat of 200-400° C. is supplied from an external heat source such as a metal heater. Besides, the existing semiconductor gas sensor lacks reliability due to inaccurate change in resistance of the gas-sensitive material because of high contact resistance between the metal of the electrode and the gas-sensing layer. In addition, it consumes a lot of power. For example, power consumption of a general existing thick-film gas sensor is about 1 mW, and that of a thin-film gas sensor based on microelectromechanical systems (MEMS) is about 10-200 mW.

REFERENCES OF THE RELATED ART

Patent Documents (Patent document 1) Korean Patent Publication No. 10-2010-0067972
(Patent document 2) Korean Patent Publication No. 10-2011-0056694

SUMMARY

The present disclosure is directed to providing a low power consumption type gas sensor self-heating and having superior gas sensitivity even when no heat is applied from outside by forming a gas-sensing layer to have a nanocolumnar structure and consuming less power, and a method for manufacturing the same.

In one general aspect, the present disclosure provides a gas sensor including: a substrate; an electrode formed on the substrate; and a gas-sensing layer formed on the electrode, wherein the gas-sensing layer is a self-heating nanocolumnar structure having nanocolumns formed on the electrode and inclined with respect to the electrode with an angle of 60-89° and gas diffusion pores formed between the nanocolumns.

The nanocolumns may be arranged on an x-y plane on the electrode such that the gas diffusion pores are formed between the nanocolumns arranged in one of the x and y directions and the nanocolumns arranged in the other direction are connected with each other. In addition, the nanocolumns may be formed to be inclined, for example, with an angle of 60-89°.

In another general aspect, the present disclosure provides a method for manufacturing a gas sensor, including: forming a gas-sensing layer of a nanocolumnar structure having gas diffusion pores formed between nanocolumns by depositing the nanocolumns on an electrode to be inclined with respect to the electrode with an angle of 60-89°.

The low power consumption type gas sensor according to the present disclosure requires no additional heater since it includes a self-heating nanocolumnar structure and exhibits superior gas sensitivity even when no heat is applied from outside. Besides, it can be produced at low cost and can be mounted on mobile devices such as mobile phones since it consumes less power.

BRIEF DESCRIPTION OF THE DRAWINGS

The above and other objects, features and advantages of the present disclosure will become apparent from the following description of certain exemplary embodiments given in conjunction with the accompanying drawings, in which.

DETAILED DESCRIPTION OF MAIN ELEMENTS

10: substrate,
20: electrode,
30: gas-sensing layer
21: first pattern of electrode,
22: second pattern of electrode,
25: electrode pad
32: nanocolumn,
34: gas diffusion pore,
32a: nucleus

DETAILED DESCRIPTION OF EMBODIMENTS

Hereinafter, exemplary embodiments will be described in detail with reference to the accompanying drawings.

The present disclosure provides a gas sensor including: a substrate; an electrode formed on the substrate; and a gas-sensing layer formed on the electrode, wherein the gas-sensing layer is a self-heating nanocolumnar structure having nanocolumns formed on the electrode and inclined with respect to the electrode with an angle of 60-89° and gas diffusion pores formed between the nanocolumns. The gas-sensing layer self-heats.

Figure 1:
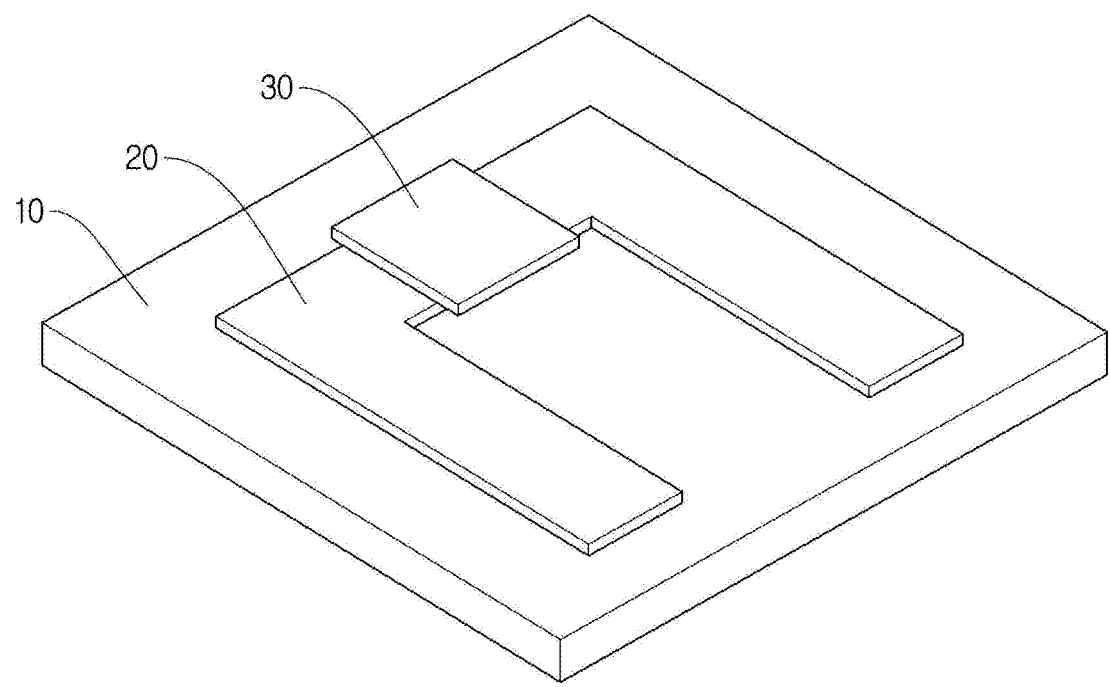
FIG. 1 is a perspective view of a gas sensor according to an exemplary embodiment of the present disclosure.

FIG. 1 shows a low power consumption type gas sensor according to an exemplary embodiment of the present disclosure. Referring to FIG. 1, a low power consumption type gas sensor includes an electrode 20 and a gas-sensing layer 30 formed on the electrode 20, along with a substrate 10 commonly included in a sensor.

The substrate 10 serves to support the electrode 20 and the gas-sensing layer 30. Specifically, the substrate 10 may be selected from a glass substrate, a sapphire substrate, a quartz substrate, an MgO substrate, a plastic film, etc., which are advantageous in terms of cost. The substrate 10 may have a thickness of, for example, 0.05-10 mm, although not being particularly limited thereto.

The electrode 20 is not particularly limited thereto as long as it is a commonly used electrode having conductivity. For example, the electrode 20 may be selected from a conductive metal oxide film, a carbon film, etc.

The metal oxide film may be a conductive oxide film containing at least one metal selected from indium (In), tin (Sn), zinc (Zn), aluminum (Al), niobium (Nb), titanium (Ti) and gallium (Ga). In specific embodiments, the electrode 20 may be an indium (indium oxide)-, tin (tin oxide)- or zinc (zinc oxide)-based conductive oxide film. More specifically, the electrode 20 may be an oxide film containing, for example, indium-doped tin oxide (ITO), fluorine-doped tin oxide (FTO), aluminum-doped zinc oxide (AZO), gallium-doped zinc oxide (GZO), indium-doped zinc oxide (IZO) or niobium-doped titanium oxide (NTO). In addition, the electrode 20 may be a conductive carbon film containing conductive carbon, e.g. graphene.

For example, the electrode 20 may have a thickness from 1 nm to 20 μm, more specifically from 10 nm to 1,000 nm.

Figure 2:
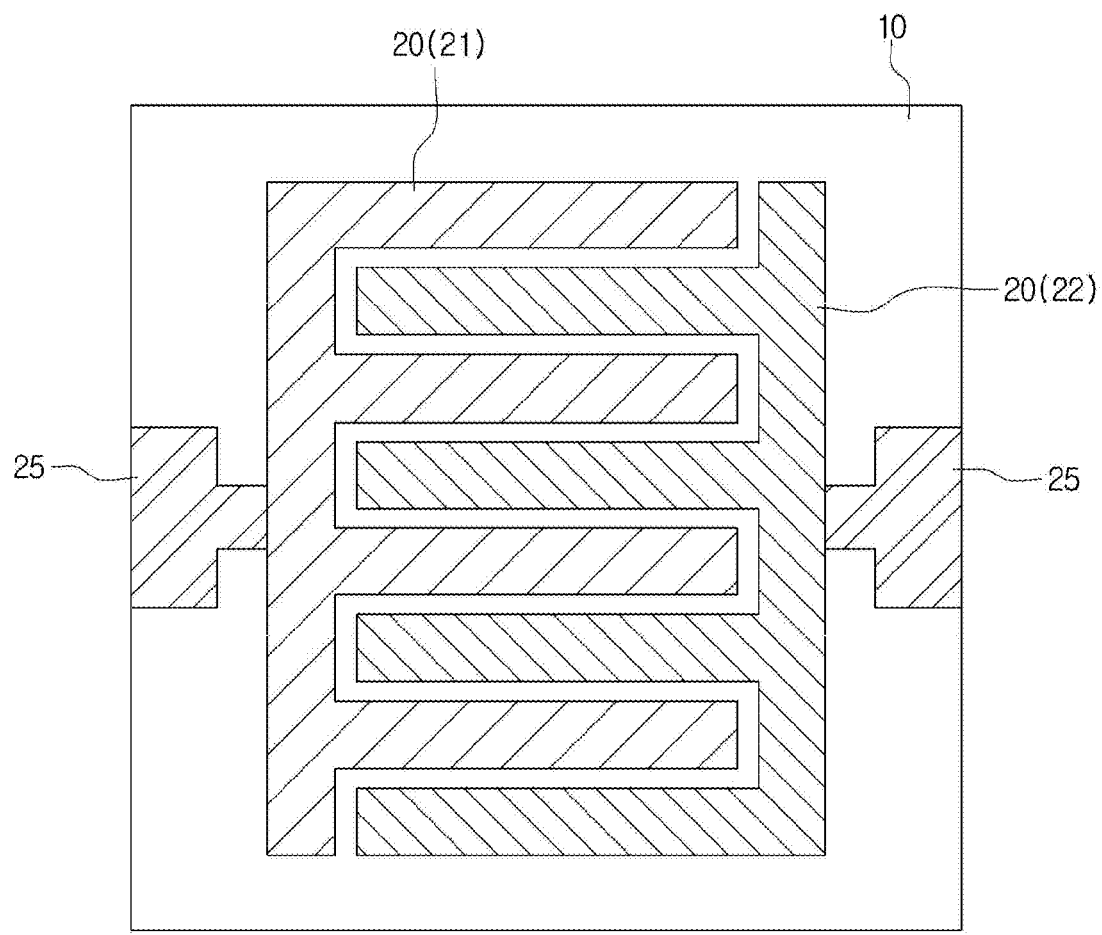
FIG. 2 is a plan view of an electrode pattern of a gas sensor according to an exemplary embodiment of the present disclosure.

The electrode 20 may be formed on the substrate 10 by deposition, e.g. sputter deposition, electron beam deposition, chemical vapor deposition or wet deposition. And, the electrode 20 may have patterns of different shapes. FIG. 2 shows an exemplary pattern of the electrode 20. As shown in FIG. 2, the electrode 20 may have an interdigitated electrode (IDE) pattern. Specifically, the electrode 20 may have a finger (or comb)-shaped first pattern 21 and a second pattern 22 interdigitating therewith formed on the substrate 10, as shown in FIG. 2.

The gas-sensing layer 30 is a layer capable of sensing gas and is formed at least partly or wholly on the electrode 20. That is to say, the gas-sensing layer 30 is formed at least partly on the electrode 20 so as to contact with the electrode 20. The gas-sensing layer 30 may be formed not only on the electrode 20 but also on the substrate 10. For example, if the electrode 20 has an IDE pattern as shown in FIG. 2, it may be formed not only on the patterned electrode 20 but also on the substrate 10 between the electrode 20 and the electrode 20.

The gas-sensing layer 30 detects gas. It is not particularly limited as long as it contains a gas-sensitive material whose electrical resistance changes in response to adsorption and oxidation/reduction of gas molecules. The gas-sensing layer 30 may be one capable of detecting the presence and/or concentration of gas.

The gas-sensing layer 30 may contain a commonly used metal oxide semiconductor material. Specifically, the gas-sensing layer 30 may contain a metal oxide with an energy band gap of at least 2.7 eV. More specifically, the gas-sensing layer 30 may contain a metal oxide with a band gap of 2.7-6.5 eV.

In an exemplary embodiment, the gas-sensing layer 30 may contain at least one metal oxide selected from tungsten oxide ($WO_3$), tin oxide ($SnO_2$), niobium oxide ($Nb_2O_5$), zinc oxide (ZnO), indium oxide ($In_2O_3$), iron oxide ($Fe_2O_3$), titanium oxide ($TiO_2$), cobalt oxide ($Co_2O_3$) and gallium oxide ($Ga_2O_3$). More specifically, it may contain tungsten oxide ($WO_3$). These metal oxides are advantageous in terms of gas sensitivity and band gap. The gas-sensing layer 30 may contain one of the metal oxides described above, a mixture of two or more of them, or a material including at least one of them.

Figure 3:
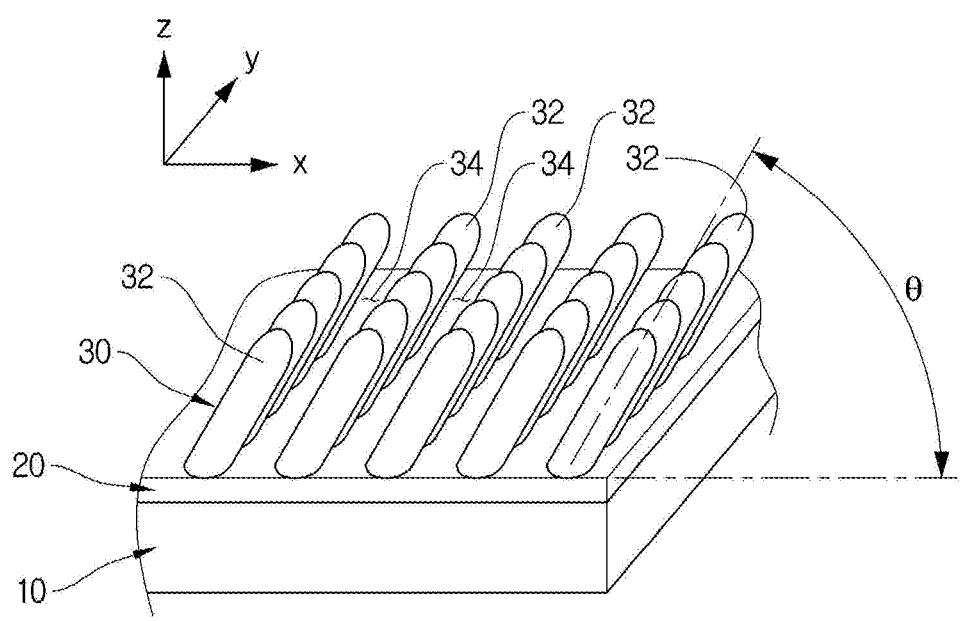
FIG. 3 is a schematic perspective view for illustrating a gas-sensing layer of a gas sensor according to an exemplary embodiment of the present disclosure.

The gas-sensing layer 30 has a nanocolumnar structure, which will be described referring to FIG. 3. FIG. 3 schematically illustrates an exemplary nanocolumnar structure.

Referring to FIG. 3, the gas-sensing layer 30 has a nanocolumnar structure including a plurality of nanocolumns 32 formed on the electrode 20 and gas diffusion pores 34 formed between the nanocolumns 32. The nanocolumns 32 are arranged on an x-y plane on the electrode 20 to protrude in a z-axis direction.

The nanocolumns 32 are formed to be inclined with respect to the electrode 20 with an angle of 60-89°. When the nanocolumns 32 are formed to have an angle θ of 60-89° with respect to the electrode 20, the volume of the pores 34 may be increased for a given thickness of the gas-sensing layer 30, i.e. for a given length (height) of the nanocolumns 32. As a result, gas may diffuse more easily and gas sensitivity may be increased. For example, the nanocolumns 32 may be formed to be inclined with an angle θ of 60-70°.

The nanocolumns 32 may be arranged on the x-y plane such that the gas diffusion pores 34 are formed between the nanocolumns 32 arranged in one of the x and y directions and the nanocolumns 32 arranged in the other direction are connected with each other. In the embodiment shown in FIG. 3, the gas diffusion pores 34 are formed between the nanocolumns 32 arranged in the x direction, and the nanocolumns 32 arranged in the y direction are connected with each other. When the individual nanocolumns are connected in one direction, the specific surface area of the gas-sensing layer may be increased and the gas-sensing layer may be provided with a self-heating effect.

For example, the nanocolumns 32 may have a thickness (diameter) not greater than 500 nm, more specifically 0.1-200 nm, although not being particularly limited thereto. And, the nanocolumns 32 may have a length (height in the z direction) not greater than 1,000 nm, more specifically 0.5-1,000 nm. And, the gas diffusion pores 34 formed between the nanocolumns 32 may have a size not greater than 500 nm, more specifically 0.1-300 nm. However, the size of the nanocolumns 32 and the pores 34 is not limited to the above description.

In the present disclosure, the gas-sensing layer 30 self-heats as it has the nanocolumnar structure in which the nanocolumns are connected in one direction. Since the nanocolumnar structure has a small contact area, when a voltage is applied, self-heating occurs in the gas-sensing layer 30 because of increased current density. Accordingly, since the gas-sensing layer of the nanocolumnar structure self-heats, no additional heater is necessary as a heat source and, thus, power consumption is decreased. In contrast, the existing thin-film sensor cannot operate at low temperatures since self-heating does not occur.

Also, the nanocolumnar structure of the gas-sensing layer 30 provides superior gas sensitivity. Specifically, the plurality of nanocolumns 32 protruding on the electrode 20 provide increased specific surface area as well as superior gas sensitivity through improved gas diffusion owing to the pores 34. That is to say, superior gas sensitivity is achieved since the gas can diffuse not only to the surface of the nanocolumns 32 but also to the bottom portion of the nanocolumns 32 through the pores 34. In particular, superior gas sensitivity can be achieved thanks to excellent response even when no heat is supplied from outside, for example, by a metal heater.

The gas-sensing layer 30 is not particularly limited as long as it has the nanocolumnar structure. Specifically, the gas-sensing layer 30 may be a single layer having the nanocolumnar structure described above or a multilayer of two or more layers with the nanocolumnar structure formed on a common thin-film gas-sensing layer. For example, the gas-sensing layer 30 may have a thickness not greater than 5 μm, specifically 1-1,000 nm, although not being limited thereto.

The gas sensor according to an exemplary embodiment of the present disclosure may further include common components. For example, it may further include an electrode pad 25 as shown in FIG. 2. The electrode pad 25 may be made of the same material as the electrode 20 and may be formed together during the deposition and patterning of the electrode 20.

Since the gas sensor according to the present disclosure requires no additional heater, if the substrate 10 and the electrode 20 are made of transparent materials and if the gas-sensing layer 30 according to the present disclosure is also made of a transparent material, the gas sensor itself may be transparent. For this, the substrate, the electrode and the gas-sensing layer may be made of transparent materials exhibiting light transmittance of at least 80%, specifically at least 90%, in the visible region. In particular, the gas-sensing layer 30 may contain a metal oxide with an energy band gap of at least 2.7 eV so as to exhibit high light transmittance in the visible region.

The low power consumption type gas sensor according to the present disclosure described above may be manufactured by various methods without particular limitation. For example, the gas sensor may be manufactured by a method described below. Hereinafter, a method for manufacturing a low power consumption type gas sensor according to an exemplary embodiment of the present disclosure will be described.

A method for manufacturing a low power consumption type gas sensor according to the present disclosure includes a step of forming a gas-sensing layer 30 of a nanocolumnar structure having gas diffusion pores formed between nanocolumns by depositing the nanocolumns on an electrode 20 to be inclined with respect to the electrode 20 with an angle of 60-89°. The materials and types of the electrode 20 and the gas-sensing layer 30 are the same as described above. The method may further include, before the step of forming the gas-sensing layer, a process of depositing the electrode on a substrate 10 (deposition process); and a process of patterning the deposited electrode (patterning process). In the deposition process, a conductive metal oxide film may be formed by, for example, sputter deposition, electron beam deposition, chemical vapor deposition or wet deposition. And, in the patterning process, the deposited metal oxide film may be patterned into an IDE pattern as shown in FIG. 2 via dry etching or wet etching.

In the step of forming the gas-sensing layer 30, the gas-sensing layer 30 is formed to have a nanocolumnar structure having nanocolumns 32 formed on the electrode 20 and gas diffusion pores 34 formed between the nanocolumns 32.

Specifically, in this second step, the gas-sensing layer 30 may be formed by deposition like the electrode 20. In this case, the overall process may be more efficient. Specifically, the gas-sensing layer 30 may be formed by sputter deposition, electron beam deposition, chemical vapor deposition or wet deposition to have the nanocolumnar structure. More specifically, sputter deposition may be used.

In the present disclosure, the contact area of the nanocolumnar structure may be controlled with the growth rate of the gas-sensing layer of the nanocolumnar structure during the deposition. Specifically, if the growth rate is relatively fast, e.g. if it exceeds 10 nm/min, the contact area decreases as the nanocolumns are separated from each other. And, if the growth rate is relatively slow, e.g. if it is below 5 nm/min, the contact area increases and it is difficult to obtain an independent nanocolumnar structure.

Specifically, the growth rate of the nanocolumns during the deposition may be 5-10 nm/min.

In the present disclosure, the deposition may be performed by sputtering. Specifically, the deposition in the present disclosure may be performed by sputtering at a partial pressure of 1-10 mTorr under Ar atmosphere with a sputtering power of 200-500 W. More specifically, it may be performed by sputtering at a partial pressure of 1-5 mTorr under 100% Ar atmosphere with a sputtering power of 300-400 W.

The gas-sensing layer 30 may be formed to have the nanocolumnar structure in various ways. For example, after disposing a mask having nanosized pores between the substrate 10 with the electrode 20 formed and a sputter gun, deposition may be performed to form the nanocolumnar structure having the nanocolumns 32 and the gas diffusion pores 34. Specifically, glancing angle deposition may be employed, the principle of which will be described referring to FIG. 4.

Figure 4:
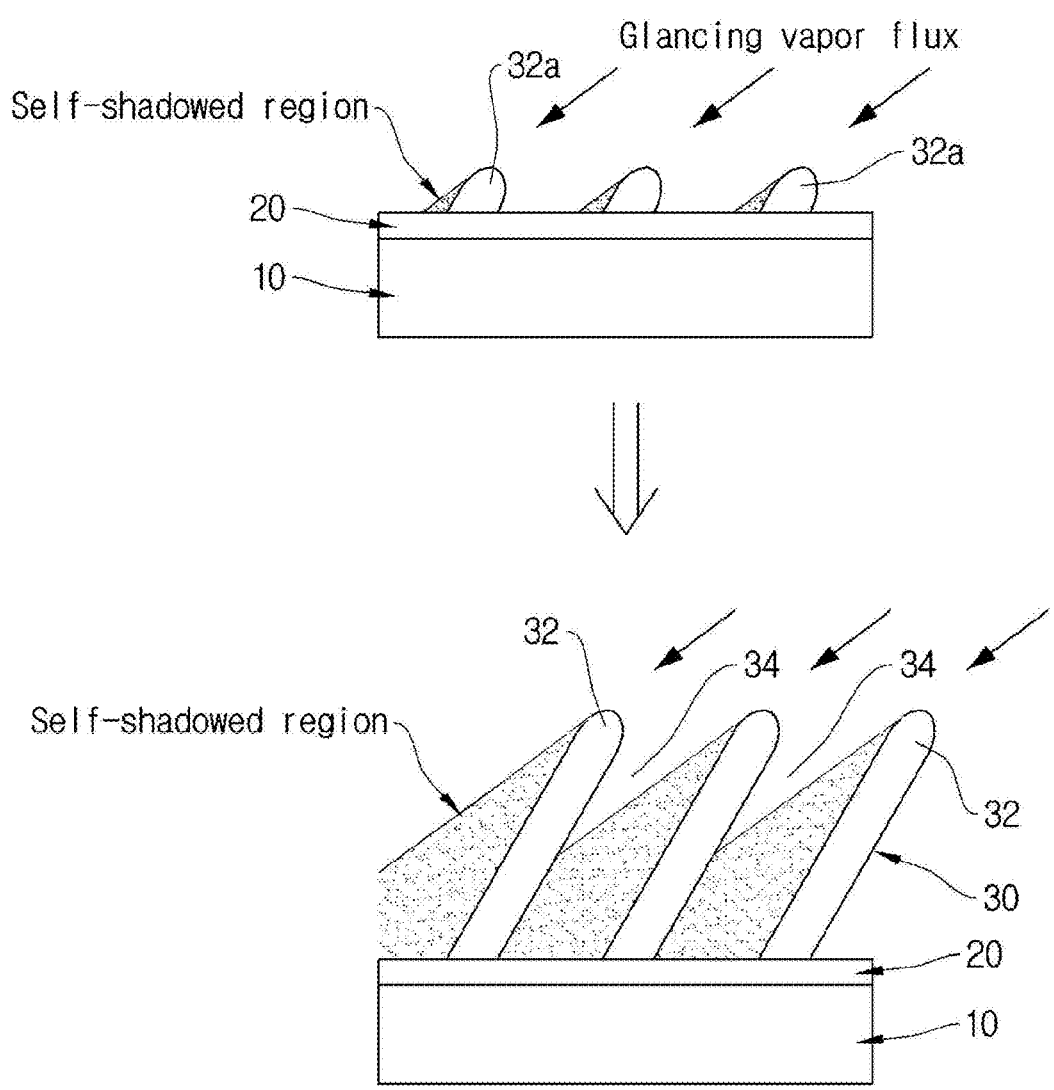
FIG. 4 is a cross-sectional view for illustrating a method for manufacturing a gas sensor according to an exemplary embodiment of the present disclosure.

Referring to FIG. 4, a metal oxide (gas-sensitive material) is deposited on the electrode 20 by sputtering such that the sputtered metal oxide flux is deposited on the electrode 20 with a predetermined angle to form metal oxide nuclei 32a. Subsequently, the metal oxide is grown on the nuclei 32a by further performing glancing angle deposition to form the nanocolumns 32. The gas diffusion pores 34 are formed between the nanocolumns 32 as a result of the self-shadowing effect. That is to say, the gas diffusion pores 34 are formed in the self-shadowed region shown in FIG. 4 since deposition by the flux does not occur there.

When depositing the metal oxide flux with a predetermined angle, the angle between the substrate 10 and the sputter gun may be maintained at 60-89°.

The low power consumption type gas sensor according to the present disclosure exhibits superior gas sensitivity while consuming less power since it self-heats owing to the nanocolumnar structure and thus requires no heater as an additional heat source. And, since the processes of forming the electrode 20 and the gas-sensing layer 30 are compatible with each other, large-scale production is possible and the gas sensor may be provided at low cost since the large-area semiconductor process can be adopted. In addition, the low power-consuming sensor can be mounted on mobile devices such as mobile phones. Besides, if all of the substrate, the electrode and the gas-sensing layer of the gas sensor according to the present disclosure are transparent, the gas sensor itself is transparent and can be easily mounted on electronic devices or windowpanes while maintaining transparency.

The examples and comparative examples of the present disclosure will now be described. The following examples are for illustrative purposes only and not intended to limit the scope of this disclosure.

EXAMPLE 1

First, a glass substrate was mounted on a sputtering apparatus. Then, indium tin oxide (ITO) film was deposited on the glass substrate by axis RF sputtering. The ITO film was deposited for about 30 minutes using a sputter gun with an ITO target comprising 90 wt % $In_2O_3$ and 10 wt % $SnO_2$ loaded, with 150 W RF power using pure argon (Ar) gas at 10 mTorr. Subsequently, the ITO film was dry etched to form a patterned electrode in the form of an interdigitated electrode (hereinafter, referred to as an 'IDE electrode').

Then, a tungsten oxide ($WO_3$) layer was deposited on the patterned IDE electrode as a gas-sensing layer by axis RF sputtering as described above. When depositing the $WO_3$ layer, the sputtering was performed at a partial pressure of 3 mTorr under 100% Ar atmosphere in a vacuum chamber with a sputtering power of 350 W, with the angle between a sputter gun with a $WO_3$ target loaded and a substrate holder maintained at about 85°. As a result, a gas sensor having $WO_3$/ITO/glass layers wherein the $WO_3$ layer has a nanocolumnar structure was manufactured.

COMPARATIVE EXAMPLE 1

A gas sensor was manufactured as in Example 1, except for forming the $WO_3$ layer as a flat thin film without having the nanocolumnar structure.

Figure 5:
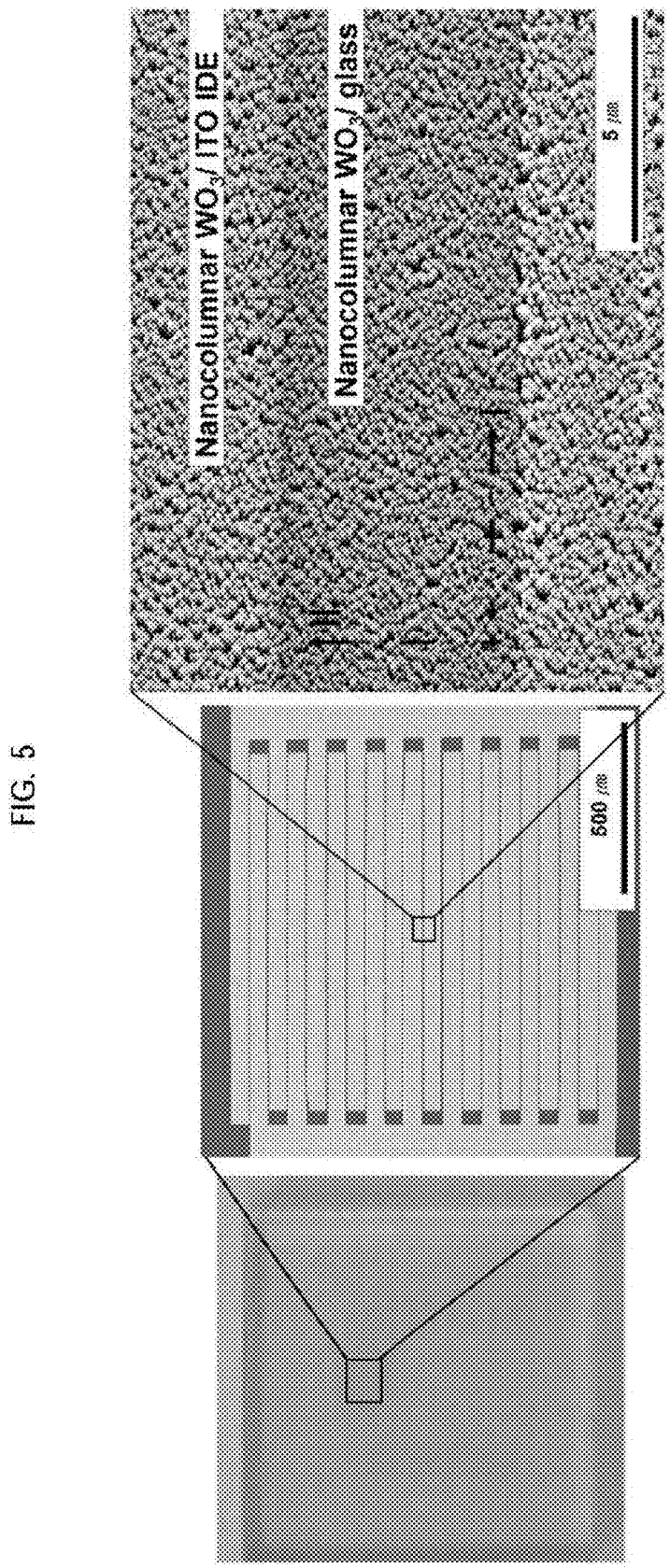
FIG. 5 shows surface images of a gas sensor manufactured according to an exemplary embodiment of the present disclosure.
Figure 6:
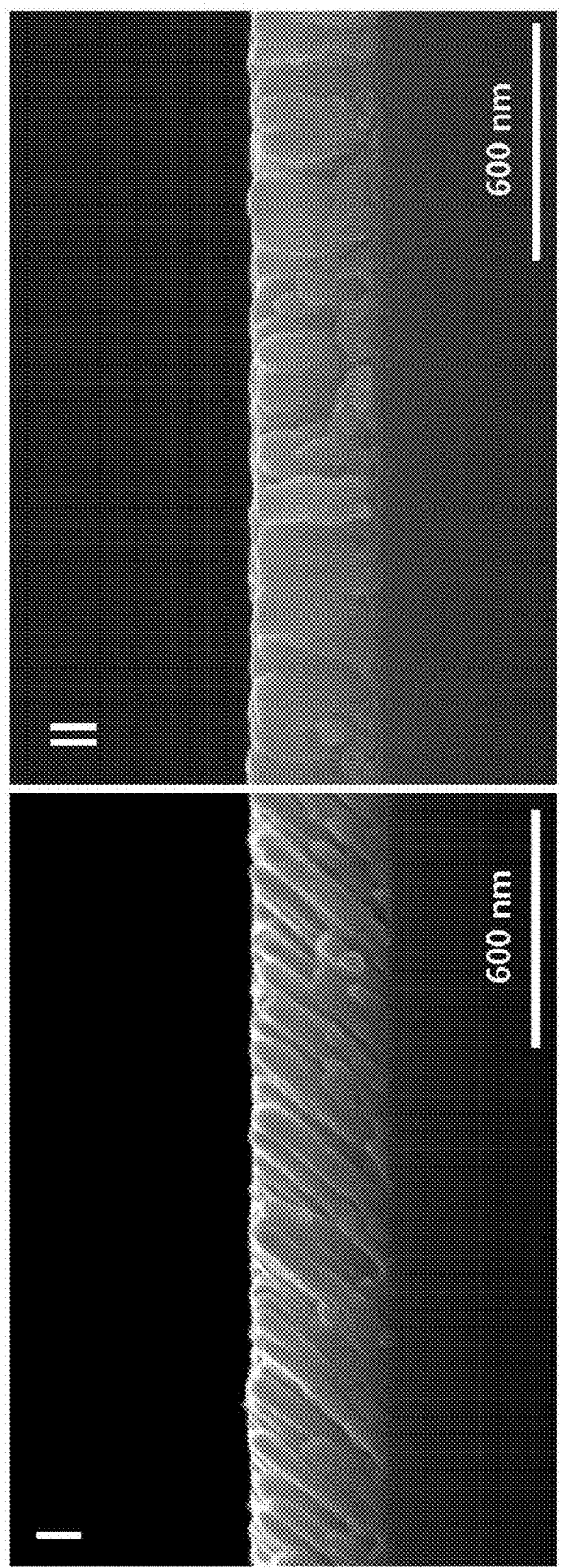
FIG. 6 shows scanning electron microscopic images of a cross-section of a gas sensor manufactured according to an exemplary embodiment of the present disclosure.

FIG. 5 and FIG. 6 show the images of the gas sensor manufactured in Example 1. FIG. 5 shows surface images and FIG. 6 shows cross-sectional scanning electron microscopic images. The left image of FIG. 6 shows the cross-section along the direction I in FIG. 5 (x direction in the x-y plane), and the right image shows the cross-section along the direction II in FIG. 5 (y direction in the x-y plane).

As seen from FIG. 5 and FIG. 6, the gas-sensing layer ($WO_3$ layer) has a nanocolumnar structure which is not appreciable with naked eyes. Also, as distinctly seen from FIG. 6, since pores are formed between the nanocolumns arranged in the direction I (x direction), gas can diffuse to the bottom portion of the $WO_3$ layer. And, the nanocolumns arranged in the direction II (y direction) are connected with each other to provide contact between the IDE electrode patterns, allowing easy measurement of electrical resistance between the IDE electrodes.

Figure 7:
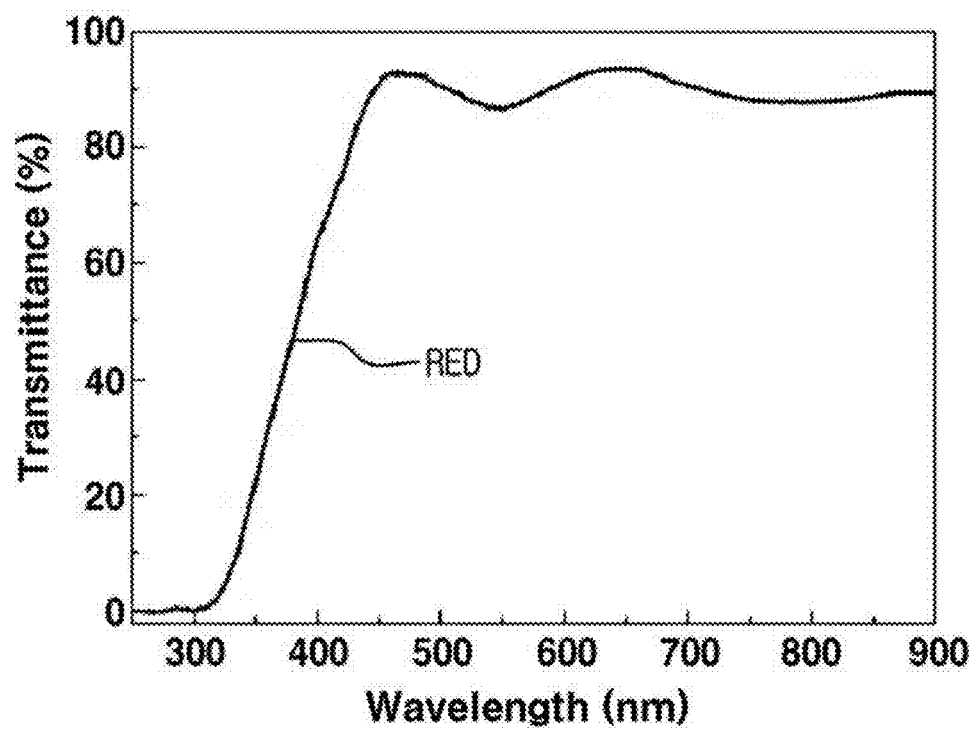
FIG. 7 shows a result of testing light transmittance of a gas sensor manufactured according to an exemplary embodiment of the present disclosure.
Figure 8:
FIG. 8 is an image of a gas sensor manufactured according to an exemplary embodiment of the present disclosure attached on the surface of a mobile terminal.

FIG. 7 shows a result of testing light transmittance of the gas sensor manufactured in Example 1. And, FIG. 8 is an image of the gas sensor manufactured in Example 1 attached on the surface of a mobile terminal.

As seen from FIG. 7, the gas sensor showed high light transmittance close to 90% in the visible region. When the gas sensor was attached on the mobile terminal, the gas sensor was not easily appreciable with naked eyes due to high light transmittance as seen from FIG. 8. Accordingly, the gas sensor can be used for displays or other applications where transparency is required such as windowpanes.

Figure 9:
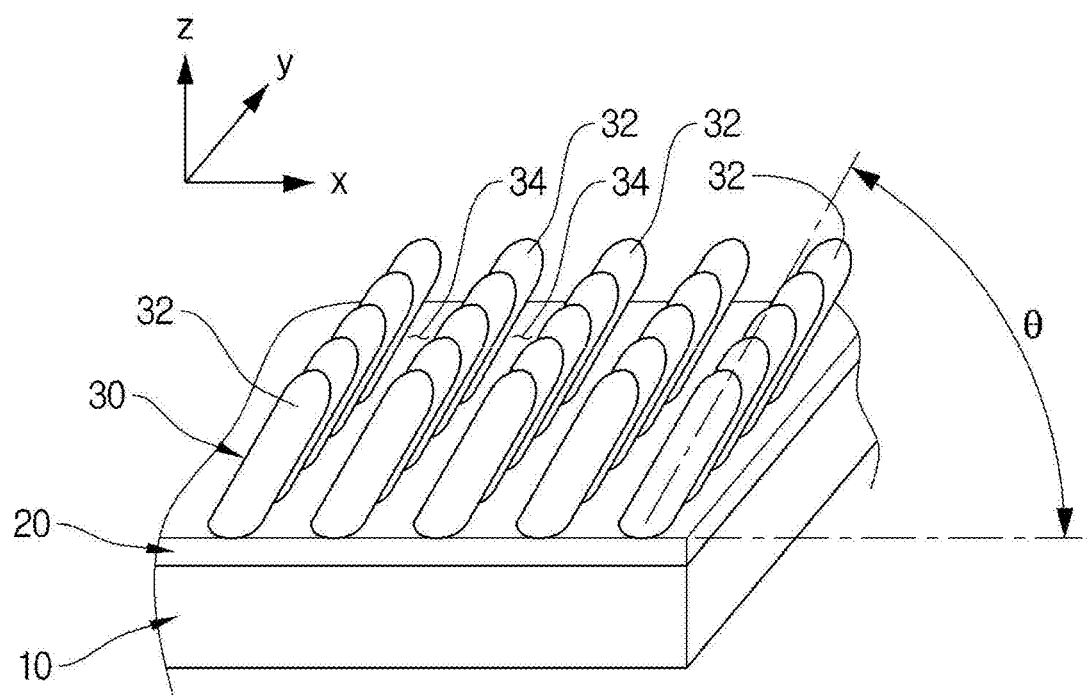
FIG. 9 shows a result of testing response of gas sensors of Example 1 and Comparative Example 1 to CO gas.
Figure 10:
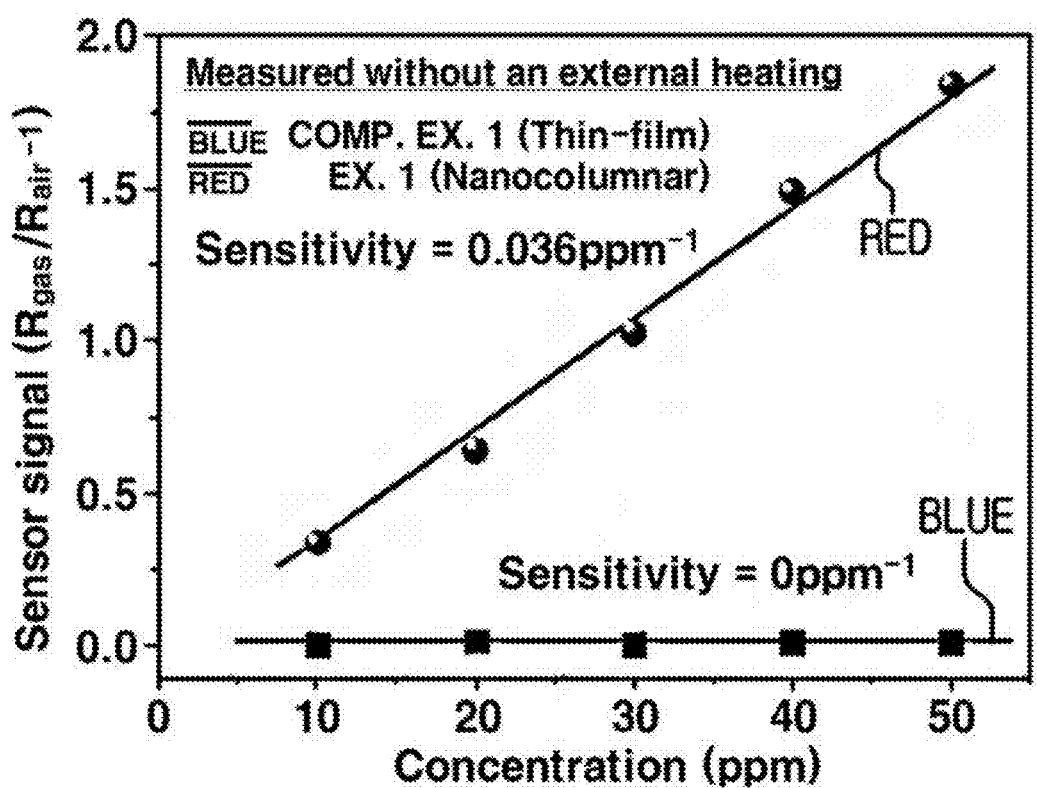
FIG. 10 shows a result of testing sensitivity of gas sensors of Example 1 and Comparative Example 1 to CO gas.

Further, response and sensitivity of the gas sensors manufactured in Example 1 and Comparative Example 1 to CO gas were tested. The result is shown in FIG. 9 and FIG. 10. FIG. 9 shows a result of testing response to CO gas, and FIG. 10 shows a result of testing sensitivity to CO gas.

First, as seen from FIG. 9, Example 1 wherein the $WO_3$ layer has a nanocolumnar structure exhibited distinct response to CO gas even under the low concentration of 10-50 ppm whereas Comparative Example 1 wherein the $WO_3$ layer is formed as a flat thin film showed no response at all.

And, as seen from FIG. 10, the sensitivity of the sensor of Comparative Example 1 wherein the $WO_3$ layer is formed as a flat thin film was 0 $ppm^{-1}$ because there was no response. In contrast, Example 1 wherein the $WO_3$ layer has a nanocolumnar structure exhibited very superior sensitivity of 0.036 $ppm^{-1}$. It is a remarkable result considering that no heat was supplied form outside during the gas detection.

During the test of response of CO gas, power consumption was 0.125 mW, which is remarkably low as compared to that of the existing semiconductor-based thick-film gas sensor (about 1 mW) or MEMS-based thin-film gas sensor (about 10-200 mW). The low power consumption suggests that the gas sensor is easily applicable to mobile devices such as mobile phones.

Figure 11:
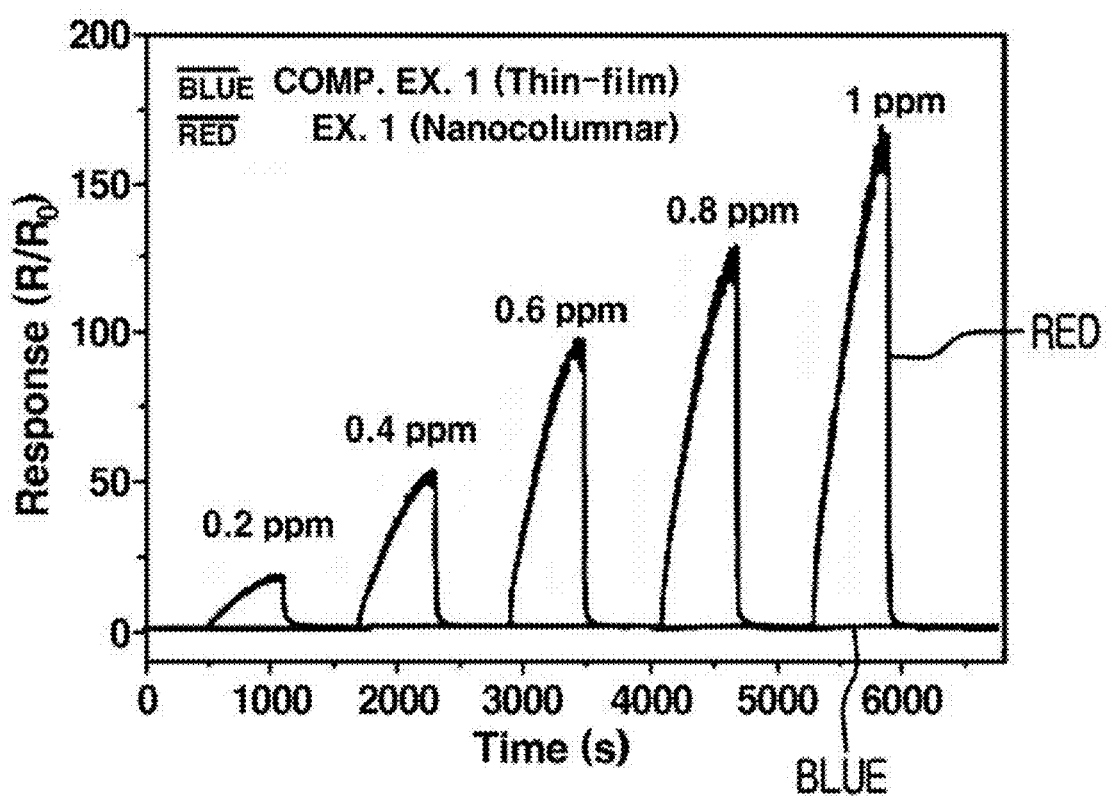
FIG. 11 shows a result of testing response of gas sensors of Example 1 and Comparative Example 1 to $NO_2$ gas.
Figure 12:
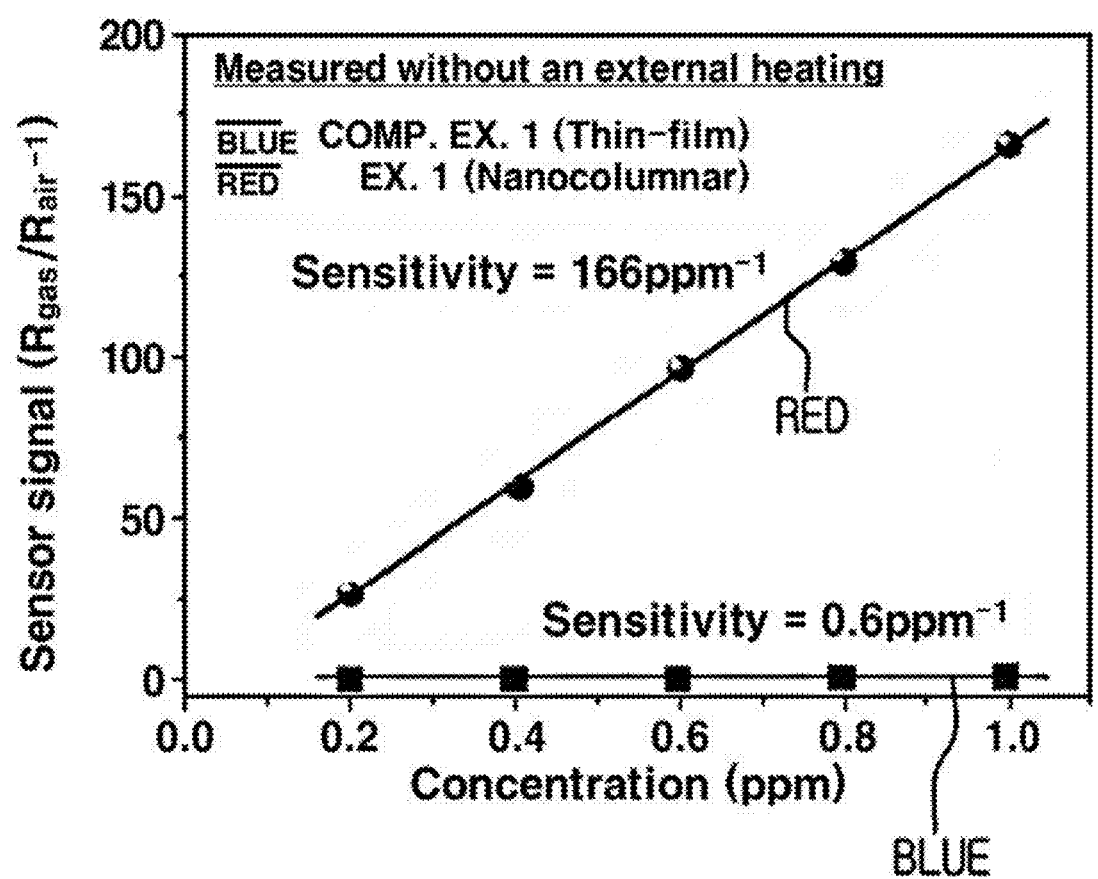
FIG. 12 shows a result of testing sensitivity of gas sensors of Example 1 and Comparative Example 1 to $NO_2$ gas.

Also, response and sensitivity of the gas sensors manufactured in Example 1 and Comparative Example 1 to $NO_2$ gas were tested. The result is shown in FIG. 11 and FIG. 12. FIG. 11 shows a result of testing response to $NO_2$ gas, and FIG. 12 shows a result of testing sensitivity to $NO_2$ gas.

First, as seen from FIG. 11, Example 1 wherein the $WO_3$ layer has a nanocolumnar structure exhibited distinct response to $NO_2$ gas even under the low concentration of 0.1-1 ppm whereas Comparative Example 1 wherein the $WO_3$ layer is formed as a flat thin film showed insignificant response.

And, as seen from FIG. 12, the sensitivity of the sensor of Comparative Example 1 wherein the $WO_3$ layer is formed as a flat thin film was 0.6 $ppm^{-1}$, suggesting that the response was insignificant. In contrast, Example 1 wherein the $WO_3$ layer has a nanocolumnar structure exhibited very superior sensitivity of 166 ppm$^{-1}$, as much as 270 times that of Comparative Example 1.

Figure 13:
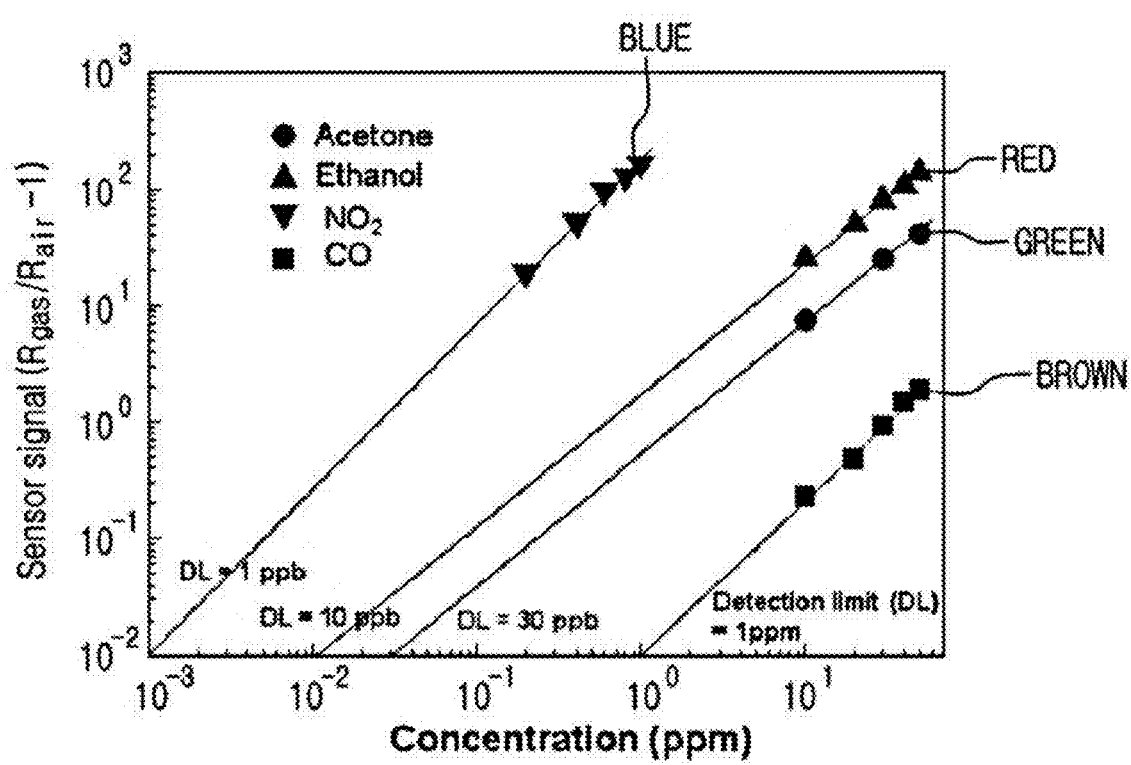
FIG. 13 shows a result of testing detection limit (DL) of a gas sensor according to an exemplary embodiment of the present disclosure for CO, $NO_2$, ethanol and acetone.

FIG. 13 shows a result of testing detection limit (DL) of the gas sensor manufactured in Example 1 for CO, NO$_2$, ethanol and acetone. The detection limit (DL) could be determined since the response to each gas changes linearly with concentration.

As seen from FIG. 13, the detection limit (DL) was very low, with 1 ppm for CO, 1 ppb for NO$_2$, 10 ppb for ethanol, and 30 ppb for acetone. This detection limit (DL) is significantly lower than the air pollution standards of Korea and the WHO [Korean standard: CO (1 hr) 25 ppm, NO$_2$ (1 hr) 100 ppb; WHO standard: CO (1 hr) 25.7 ppm, NO$_2$ (1 hr) 105 ppb].

From the detection limit test result, it can be seen that the gas sensor can be used not only as an air quality sensor for detecting CO, NO$_x$, H$_2$, H$_2$O, SO$_2$, NH$_3$, O$_3$, H$_2$S and volatile organic compounds (VOCs) but also as a sensor for detecting other harmful gas or toxic gas for counter-terrorism.

EXAMPLES 2-5

Gas sensors were manufactured as in Example 1 by varying the materials of a gas-sensing layer. Specifically, when forming the gas-sensing layer having a nanocolumnar structure on an IDE electrode by sputtering, different targets were used to form SnO$_2$ layer (Example 2), Nb$_2$O$_5$ layer (Example 3), ZnO layer (Example 4) and In$_2$O$_3$ layer (Example 5) as the gas-sensing layer having the nanocolumnar structure on the IDE electrode.

COMPARATIVE EXAMPLES 2-5

Gas sensors were manufactured as in Comparative Example 1 by varying the materials of a gas-sensing layer. Specifically, different targets were used to form SnO$_2$ layer (Comparative Example 2), Nb$_2$O$_5$ layer (Comparative Example 3), ZnO layer (Comparative Example 4) and In$_2$O$_3$ layer (Comparative Example 5) as the gas-sensing layer having the flat thin film on the IDE electrode.

Figure 14:
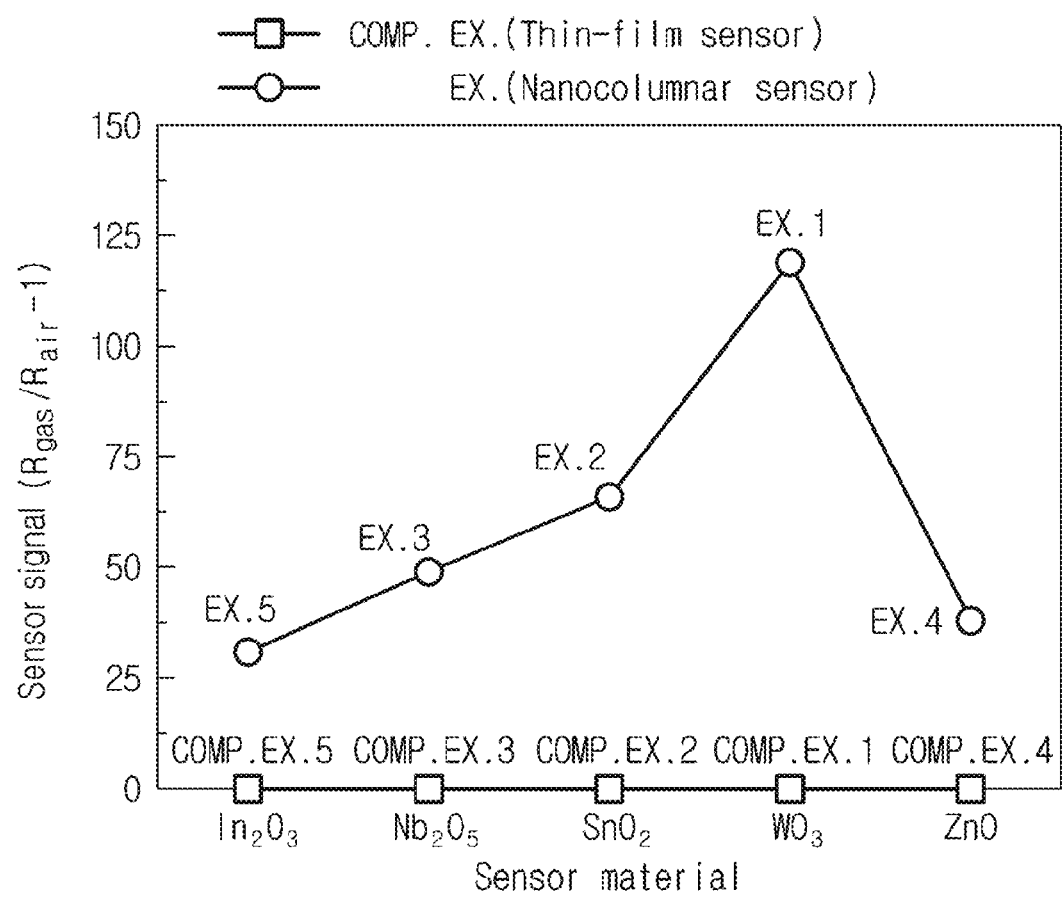
FIG. 14 shows a result of testing response of gas sensors of Examples 1-5 and Comparative Examples 1-5 with different gas-sensing layers to $NO_2$ gas (0.8 ppm).

Response of the gas sensors manufactured in Examples 2-5 and Comparative Examples 2-5 to NO$_2$ gas (0.8 ppm) was tested. The result is shown in FIG. 14. The test result for Example 1 (WO$_3$) and Comparative Example 1 (WO$_3$) is also given in FIG. 14.

As seen from FIG. 14, Examples 1-5 wherein the gas-sensing layer has a nanocolumnar structure exhibited distinct response to NO$_2$ gas (0.8 ppm) whereas Comparative Examples 1-5 wherein the gas-sensing layer is formed as a flat thin film showed insignificant response to NO$_2$ gas (0.8 ppm).

As demonstrated through the above examples, the gas sensor wherein the gas-sensing layer has a nanocolumnar structure exhibits excellent response as well as very superior gas sensitivity. By forming the gas-sensing layer to have the nanocolumnar structure via a simple process, very superior gas sensitivity can be achieved even when no heat is supplied from outside. Also, since the gas sensor can be made to be highly transparent with light transmittance of at least 90% in the visible region, it is applicable to displays or other applications where transparency is required such as windowpanes. In addition, since it consumes less power, it can be used for mobile devices such as mobile phones.

In addition, the gas sensor can be produced in large scale since both the electrode and the gas-sensing layer contain metal oxides and can be formed by the same deposition process. Besides, since the gas sensor does not require the expensive noble metal electrode and the production process is compatible, it can be produced at low cost.

While the present disclosure has been described with respect to the specific embodiments, it will be apparent to those skilled in the art that various changes and modifications may be made without departing from the spirit and scope of the disclosure as defined in the following claims.

What is claimed is:

1. A gas sensor comprising:
   a substrate;
   an electrode formed on the substrate; and
   a gas-sensing layer formed on the electrode,
   wherein the gas-sensing layer is a self-heating nanocolumnar structure having nanocolumns formed on the electrode and inclined with respect to the electrode with an angle of 60-89° and gas diffusion pores formed between the nanocolumns.

2. The gas sensor according to claim 1, wherein the nanocolumns are arranged on an x-y plane on the electrode such that the gas diffusion pores are formed between the nanocolumns arranged in one of the x and y directions and the nanocolumns arranged in the other direction are connected with each other.

3. The gas sensor according to claim 1, wherein the nanocolumns are formed by glancing angle deposition and the gas diffusion pores are formed in the self-shadowed region between the nanocolumns.

4. The gas sensor according to claim 1, wherein the gas-sensing layer comprises a metal oxide having a band gap of at least 2.7 eV.

5. The gas sensor according to claim 1, wherein the gas-sensing layer comprises at least one metal oxide selected from tungsten oxide (WO$_3$), tin oxide (SnO$_2$), niobium oxide (Nb$_2$O$_5$), zinc oxide (ZnO), indium oxide (In$_2$O$_3$), iron oxide (Fe$_2$O$_3$), titanium oxide (TiO$_2$), cobalt oxide (Co$_2$O$_3$) and gallium oxide (Ga$_2$O$_3$).

6. The gas sensor according to claim 1, wherein the substrate is a glass, sapphire, quartz or MgO substrate.

7. The gas sensor according to claim 1, wherein the electrode is a metal film, a metal oxide film or a carbon film.

8. The gas sensor according to claim 7, wherein the electrode is a metal film and the metal film comprises at least one selected from copper (Cu), gold (Au), silver (Ag) and platinum (Pt).

9. The gas sensor according to claim 7, wherein the electrode is a metal oxide film and the metal oxide film is an oxide film comprising at least one metal selected from indium (In), tin (Sn), zinc (Zn), aluminum (AD, niobium (Nb), titanium (Ti) and gallium (Ga).

10. The gas sensor according to claim 7, wherein the electrode is a metal oxide film and the metal oxide film is an oxide film selected from indium-doped tin oxide (ITO), fluorine-doped tin oxide (FTC)), aluminum-doped zinc oxide (AZO), gallium-doped zinc oxide (GZO), indium-doped zinc oxide (IZO) and niobium-doped titanium oxide (NTO).

11. The gas sensor according to claim 7, wherein the electrode is a carbon film and the carbon film comprises graphene.

12. The gas sensor according to claim 1, wherein the electrode is a metal oxide film or a carbon film and the gas sensor has a light transmittance of at least 90% in the visible region.

* * * * *